(12) United States Patent
Safran et al.

(10) Patent No.: US 9,597,412 B2
(45) Date of Patent: Mar. 21, 2017

(54) INJECTABLE DELIVERY SYSTEM FOR HEPARAN-BINDING GROWTH FACTORS

(75) Inventors: Catherine E. Safran, Bear, DE (US); Mary C. Farach-Carson, Houston, TX (US); Xinqiao Jia, Newark, DE (US); Padma P. Srinivasan, Newark, DE (US); Amit Jha, Oakland, CA (US)

(73) Assignee: University of Delaware, Newark, DE (US)

( * ) Notice: Subject to any disclaimer, the term of this patent is extended or adjusted under 35 U.S.C. 154(b) by 197 days.

(21) Appl. No.: 14/004,944

(22) PCT Filed: Mar. 16, 2012

(86) PCT No.: PCT/US2012/029411
§ 371 (c)(1),
(2), (4) Date: Sep. 13, 2013

(87) PCT Pub. No.: WO2012/125914
PCT Pub. Date: Sep. 20, 2012

(65) Prior Publication Data
US 2014/0005111 A1    Jan. 2, 2014

Related U.S. Application Data

(60) Provisional application No. 61/453,340, filed on Mar. 16, 2011.

(51) Int. Cl.

| | |
|---|---|
| *A61K 38/18* | (2006.01) |
| *A61K 47/48* | (2006.01) |
| *A61K 9/14* | (2006.01) |
| *A61P 19/02* | (2006.01) |
| *A61L 27/52* | (2006.01) |
| *A61L 27/54* | (2006.01) |
| *A61K 9/00* | (2006.01) |
| *A61K 45/06* | (2006.01) |
| *A61K 38/19* | (2006.01) |
| *A61L 27/26* | (2006.01) |

(52) U.S. Cl.
CPC ...... *A61K 47/48784* (2013.01); *A61K 9/0019* (2013.01); *A61K 38/18* (2013.01); *A61K 38/1875* (2013.01); *A61K 38/19* (2013.01); *A61K 45/06* (2013.01); *A61K 47/48246* (2013.01); *A61L 27/26* (2013.01); *A61L 27/52* (2013.01); *A61L 27/54* (2013.01); *A61L 2300/414* (2013.01); *A61L 2400/06* (2013.01); *A61L 2430/06* (2013.01)

(58) Field of Classification Search
None
See application file for complete search history.

(56) References Cited

U.S. PATENT DOCUMENTS

| | | |
|---|---|---|
| 7,345,035 B2 | 3/2008 | Taber et al. |
| 7,368,126 B2 | 5/2008 | Chen et al. |
| 7,671,018 B2 | 3/2010 | Carson et al. |
| 7,803,905 B2 | 9/2010 | Farach-Carson et al. |
| 7,875,591 B2 | 1/2011 | Carson et al. |
| 7,897,727 B2 | 3/2011 | Farach-Carson et al. |
| 8,124,120 B2 | 2/2012 | Sadozai et al. |
| 2004/0063619 A1* | 4/2004 | Carson et al. .......... 514/8 |
| 2007/0099828 A1 | 5/2007 | Bobadilla |
| 2009/0074889 A1 | 3/2009 | Amador et al. |
| 2009/0162436 A1 | 6/2009 | Carson et al. |
| 2010/0021934 A1 | 1/2010 | Farach-Carson |
| 2010/0221302 A1 | 9/2010 | Carson et al. |
| 2010/0291045 A1 | 11/2010 | Jia et al. |
| 2011/0082081 A1 | 4/2011 | Carson et al. |

FOREIGN PATENT DOCUMENTS

| | | |
|---|---|---|
| RU | 2006122632 A | 2/2008 |
| RU | 2 351 367 C2 | 4/2009 |
| RU | 2 355 385 C2 | 5/2009 |

OTHER PUBLICATIONS

Rosenbloom et al., Biochim. Biophys. Acta., 2013, vol. 1832:1088-1103.*
Kapoor et al., Nat. Rev. Rheumatol., 2011, vol. 7(1):33-42 (Abstract).*
Jha et al., Biomaterials, 2009, vol. 30(36):6964-6975.*
American College of Rheumatology Subcommittee on Osteoarthritis Guidelines, Arthritis Rheum., 2000, vol. 43(9):1905-1915.*
Costell et al., Eur. J. Biochem, 243:115-121 (1997).
Jha et al., Biomaterials, 30:6964-75 (2009).
Yang et al., Tissue Eng., 11:76-89 (2005).
PCT/US2012/029411 International Search Report by N. Litvinenko mailed Jul. 12, 2012.

* cited by examiner

*Primary Examiner* — Xiaozhen Xie
(74) *Attorney, Agent, or Firm* — RatnerPrestia

(57) ABSTRACT

A method for enhancing chondrogenesis in a subject in need thereof comprises administering to the subject an effective amount of a pharmaceutical composition comprising a growth factor bound to hyaluronic acid (HA)-based hydrogel particles (HGPs). The hyaluronic acid (HA)-based hydrogel particles (HGPs) are conjugated with a heparan sulfate proteoglycan (HSPG). Related medicaments and methods for preparing the medicaments are provided.

14 Claims, 5 Drawing Sheets

Figure 1

A.  SEQ ID NO: 1 (human, aa#22-193 genbank# NP_005520):

VTHGLRAYDGLSLPEDIETVTASQMRWTHSYLSDDEYMLADSISGDDLGSGDLGSG
DFQMVYFRALVNFTRSIEYSPQLEDAGSREFREVSEAVVDTLESEYLKIPGDQVVSVV
FIKELDGWVFVELDVGSEGNADGAQIQEMLLRVISSGSVASYVTSPQGFQFRRLGTV
P

B.  SEQ ID NO: 2 (mouse, aa#22-194 genbank# NP_032331):

VTHGLRAYDGLSLPEDTETVTASRYGWTYSYLSDDEDLLADDASGDGLGSGDVGSG
DFQMVYFRALVNFTRSIEYSPQLEDASAKEFREVSEAVVEKLEPEYRKIPGDQIVSVV
FIKELDGWVFVELDVGSEGNADGSQIQEVLHTVVSSGSIGPYVTSPWGFKFRRLGTV
PQ

C.  SEQ ID NO: 3 (cow, aa#12-183, genbank# DAA32243)

VTHGLRAYDGLSLPEDAETVTAGRAGWSYSDLSDDEDFLADEASGDGVGSGDLGSG
DFQMVYFRALVNFTHSIDYSPQLEDAGSEEFREVSEAVVDTLESEYLKIPGDQVVSV
VFIKELDGWVFVELDVGSEGNADGAQIQEVLHGVISSGSIASYVTSPQGFQFRRLGTV
P

D.  SEQ ID NO: 4 (rabbit, aa#68-239, genbank# XP_002716087)

VAHGLRAYEGLSLPEDTETVTEGRAGWSYSYLSDDEDLLADDASGDGLGSGDLGSG
DFQMVYFRALVNFTHSIEYSPRLEDAGSREFREVSDAVVDKLEMEYAKIPGDQVVSV
VFIKELDGWVFVELDVGSEGNADGAQIQDVLHRVVSGGAIASYVTSPQGFQFRRLGT
VP

E.  SEQ ID NO: 5 (chicken, aa#28-193, genbank# NP_001001876)

SFPEDTVADHVGSTWRRRYYAQLSDDEDLLADEASADGSGELGSGDVALVALAPTV
YFRALVNFTRSIDFSPRLEDPNSEEFREVSEAVVDTLESEYYKIPGEQMVSVVFIKELE
GSVFVELDVGSEGNGDEAQIGAVLRSVVTAGSIASFVTSPVGFQFRRLGAV

SEQUENCE LISTING

```
<160> NUMBER OF SEQ ID NOS: 5

<210> SEQ ID NO 1
<211> LENGTH: 172
<212> TYPE: PRT
<213> ORGANISM: Homo sapiens

<400> SEQUENCE: 1

Val Thr His Gly Leu Arg Ala Tyr Asp Gly Leu Ser Leu Pro Glu Asp
1               5                   10                  15

Ile Glu Thr Val Thr Ala Ser Gln Met Arg Trp Thr His Ser Tyr Leu
            20                  25                  30

Ser Asp Asp Glu Tyr Met Leu Ala Asp Ser Ile Ser Gly Asp Asp Leu
        35                  40                  45

Gly Ser Gly Asp Leu Gly Ser Gly Asp Phe Gln Met Val Tyr Phe Arg
    50                  55                  60

Ala Leu Val Asn Phe Thr Arg Ser Ile Glu Tyr Ser Pro Gln Leu Glu
65                  70                  75                  80

Asp Ala Gly Ser Arg Glu Phe Arg Glu Val Ser Glu Ala Val Val Asp
                85                  90                  95

Thr Leu Glu Ser Glu Tyr Leu Lys Ile Pro Gly Asp Gln Val Val Ser
            100                 105                 110

Val Val Phe Ile Lys Glu Leu Asp Gly Trp Val Phe Val Glu Leu Asp
        115                 120                 125

Val Gly Ser Glu Gly Asn Ala Asp Gly Ala Gln Ile Gln Glu Met Leu
    130                 135                 140

Leu Arg Val Ile Ser Ser Gly Ser Val Ala Ser Tyr Val Thr Ser Pro
145                 150                 155                 160

Gln Gly Phe Gln Phe Arg Arg Leu Gly Thr Val Pro
                165                 170

<210> SEQ ID NO 2
<211> LENGTH: 173
<212> TYPE: PRT
<213> ORGANISM: Mus musculus

<400> SEQUENCE: 2

Val Thr His Gly Leu Arg Ala Tyr Asp Gly Leu Ser Leu Pro Glu Asp
1               5                   10                  15

Thr Glu Thr Val Thr Ala Ser Arg Tyr Gly Trp Thr Tyr Ser Tyr Leu
            20                  25                  30

Ser Asp Asp Glu Asp Leu Leu Ala Asp Ala Ser Gly Asp Gly Leu
        35                  40                  45

Gly Ser Gly Asp Val Gly Ser Gly Asp Phe Gln Met Val Tyr Phe Arg
    50                  55                  60

Ala Leu Val Asn Phe Thr Arg Ser Ile Glu Tyr Ser Pro Gln Leu Glu
65                  70                  75                  80

Asp Ala Ser Ala Lys Glu Phe Arg Glu Val Ser Glu Ala Val Val Glu
```

```
                85                  90                  95
Lys Leu Glu Pro Glu Tyr Arg Lys Ile Pro Gly Asp Gln Ile Val Ser
            100                 105                 110
Val Val Phe Ile Lys Glu Leu Asp Gly Trp Val Phe Val Glu Leu Asp
            115                 120                 125
Val Gly Ser Glu Gly Asn Ala Asp Gly Ser Gln Ile Gln Glu Val Leu
        130                 135                 140
His Thr Val Val Ser Ser Gly Ser Ile Gly Pro Tyr Val Thr Ser Pro
145                 150                 155                 160
Trp Gly Phe Lys Phe Arg Arg Leu Gly Thr Val Pro Gln
                165                 170
```

<210> SEQ ID NO 3
<211> LENGTH: 172
<212> TYPE: PRT
<213> ORGANISM: Bos taurus

<400> SEQUENCE: 3

```
Val Thr His Gly Leu Arg Ala Tyr Asp Gly Leu Ser Leu Pro Glu Asp
1               5                   10                  15
Ala Glu Thr Val Thr Ala Gly Arg Ala Gly Trp Ser Tyr Ser Asp Leu
            20                  25                  30
Ser Asp Asp Glu Asp Phe Leu Ala Asp Glu Ala Ser Gly Asp Gly Val
        35                  40                  45
Gly Ser Gly Asp Leu Gly Ser Gly Asp Phe Gln Met Val Tyr Phe Arg
    50                  55                  60
Ala Leu Val Asn Phe Thr His Ser Ile Asp Tyr Ser Pro Gln Leu Glu
65                  70                  75                  80
Asp Ala Gly Ser Glu Glu Phe Arg Glu Val Ser Glu Ala Val Val Asp
                85                  90                  95
Thr Leu Glu Ser Glu Tyr Leu Lys Ile Pro Gly Asp Gln Val Val Ser
            100                 105                 110
Val Val Phe Ile Lys Glu Leu Asp Gly Trp Val Phe Val Glu Leu Asp
            115                 120                 125
Val Gly Ser Glu Gly Asn Ala Asp Gly Ala Gln Ile Gln Glu Val Leu
        130                 135                 140
His Gly Val Ile Ser Ser Gly Ser Ile Ala Ser Tyr Val Thr Ser Pro
145                 150                 155                 160
Gln Gly Phe Gln Phe Arg Arg Leu Gly Thr Val Pro
                165                 170
```

<210> SEQ ID NO 4
<211> LENGTH: 172
<212> TYPE: PRT
<213> ORGANISM: Oryctolagus cuniculus

<400> SEQUENCE: 4

```
Val Ala His Gly Leu Arg Ala Tyr Glu Gly Leu Ser Leu Pro Glu Asp
1               5                   10                  15
Thr Glu Thr Val Thr Glu Gly Arg Ala Gly Trp Ser Tyr Ser Tyr Leu
            20                  25                  30
Ser Asp Asp Glu Asp Leu Leu Ala Asp Ala Ser Gly Asp Gly Leu
        35                  40                  45
Gly Ser Gly Asp Leu Gly Ser Gly Asp Phe Gln Met Val Tyr Phe Arg
    50                  55                  60
Ala Leu Val Asn Phe Thr His Ser Ile Glu Tyr Ser Pro Arg Leu Glu
```

```
                    65                  70                  75                  80
Asp Ala Gly Ser Arg Glu Phe Arg Glu Val Ser Asp Ala Val Val Asp
                85                  90                  95

Lys Leu Glu Met Glu Tyr Ala Lys Ile Pro Gly Asp Gln Val Val Ser
                100                 105                 110

Val Val Phe Ile Lys Glu Leu Asp Gly Trp Val Phe Val Glu Leu Asp
                115                 120                 125

Val Gly Ser Glu Gly Asn Ala Asp Gly Ala Gln Ile Gln Asp Val Leu
                130                 135                 140

His Arg Val Val Ser Gly Gly Ala Ile Ala Ser Tyr Val Thr Ser Pro
145                 150                 155                 160

Gln Gly Phe Gln Phe Arg Arg Leu Gly Thr Val Pro
                165                 170

<210> SEQ ID NO 5
<211> LENGTH: 166
<212> TYPE: PRT
<213> ORGANISM: Gallus gallus

<400> SEQUENCE: 5

Ser Phe Pro Glu Asp Thr Val Ala Asp His Val Gly Ser Thr Trp Arg
1               5                   10                  15

Arg Arg Tyr Tyr Ala Gln Leu Ser Asp Glu Asp Leu Leu Ala Asp
                20                  25                  30

Glu Ala Ser Ala Asp Gly Ser Gly Glu Leu Gly Ser Gly Asp Val Ala
                35                  40                  45

Leu Val Ala Leu Ala Pro Thr Val Tyr Phe Arg Ala Leu Val Asn Phe
    50                  55                  60

Thr Arg Ser Ile Asp Phe Ser Pro Arg Leu Glu Asp Pro Asn Ser Glu
65                  70                  75                  80

Glu Phe Arg Glu Val Ser Glu Ala Val Val Asp Thr Leu Glu Ser Glu
                85                  90                  95

Tyr Tyr Lys Ile Pro Gly Glu Gln Met Val Ser Val Phe Ile Lys
                100                 105                 110

Glu Leu Glu Gly Ser Val Phe Val Glu Leu Asp Val Gly Ser Glu Gly
                115                 120                 125

Asn Gly Asp Glu Ala Gln Ile Gly Ala Val Leu Arg Ser Val Val Thr
                130                 135                 140

Ala Gly Ser Ile Ala Ser Phe Val Thr Ser Pro Val Gly Phe Gln Phe
145                 150                 155                 160

Arg Arg Leu Gly Ala Val
                165
```

INJECTABLE DELIVERY SYSTEM FOR HEPARAN-BINDING GROWTH FACTORS

CROSS-REFERENCE TO RELATED APPLICATION

This application is a U.S. National Phase Application of PCT International Application PCT/US2012/029411, filed Mar. 16, 2012, which claims the benefit of U.S. Provisional Application No. 61/453,340, filed Mar. 16, 2011, the contents of each of which are incorporated herein in their entireties for all purposes.

GOVERNMENT INTERESTS

This invention was made with government support under Grant Nos. P20-RR016458 and R01 DC008965 awarded by the National Institutes of Health (NIH). The government has certain rights in this invention.

FIELD OF THE INVENTION

The invention relates generally to methods and medicaments useful for enhancing chondrogenesis in a subject.

BACKGROUND OF THE INVENTION

Articular cartilage is a viscoelastic tissue essential for the absorption of shocks and distribution of loads. Because of its non-vascularized, non-innervated and sparsely cell populated nature, this tissue displays poor regenerative capacity. Recently, growth factor therapy has emerged as a novel strategy for enhancing chondrogenic differentiation and repairing functional cartilage. The heparan sulfate binding growth factor (HBGF) bone morphogenetic protein 2 (BMP2), which plays a critical role in the establishment of normal cartilage during development, also was found to enhance the differentiated phenotype of mesenchymal stem cells in culture. In addition, several studies indicate that BMP2 expression is elevated in damaged and/or mechanically-challenged cartilage during the early stages of osteoarthritis (OA). This increase in BMP2 levels is believed to enhance reparative processes and reactivate morphogenetic pathways including synthesis of extracellular matrix (ECM) components. During disease progression, the weakened synthetic machinery of chondrocytes eventually becomes unable to compensate for the degradation of ECM components leading to degenerative OA. Therefore, it is apparent that supplementing BMP2 at the initial stages of OA may have a significant inhibitory effect on the development of OA. Nonetheless, even with the high chondrogenic potency of BMP2, the biggest challenge lies in developing an efficient delivery system to counteract its short half life and rapid degradation in vivo.

Perlecan/HSPG2 is a heparan sulfate proteoglycan (HSPG) that represents an essential component of cartilage ECM. The NH2-terminal portion of perlecan (domain 1 or PlnD1) carrying HS chains specifically binds HBGFs through three consensus serine-glycine-aspartate (SGD) motifs and enhances their interaction with the cognate signal transducing receptor to stimulate biological processes. Thus, PlnD1 can act as a depot for BMP2 storage and controlled release, protect it from proteolytic degradation and potentiate its biological activity. Previous studies demonstrate that PlnD1 can be successfully used in vitro to modulate the chondrogenic bioactivity of BMP2. However, because of its own diffusion and susceptibility to degradation, PlnD1 only can be effectively used as a HBGF reservoir for in vivo cartilage repair if immobilized through conjugation to a larger biocompatible carrier.

A stable biomimetic HBGF delivery system has been developed by conjugating PlnD1 to hyaluronic acid (HA)-based microgels (PlnD1-HA). Previous in vitro study using PlnD1-HA microgels demonstrated a near zero-order release kinetic of BMP2 from this biomaterial along with enhanced chondrocytic differentiation with ECM production. HA is a natural component of articular cartilage that functions as a matrix organizer by interacting with other matrix molecules such as aggrecan. HA-based macromolecules also commonly are used in the clinic as viscosupplements to enhance joint mobility and provide temporary relief of knee pain by increasing the viscosity and elasticity of synovial fluid. However, HA alone does not promote the regeneration of cartilage ECM and is traditionally not administered in combination with active cartilage repair agents. Thus, increased physical activity after palliative injection of HA often results in long term adverse effects and accelerates disease progression.

Thus, there remains a need for an effective and safe delivery system for HBGFs to enhance chondrogenesis in subjects, especially those who have suffered and/or are predisposed to cartilage damage.

SUMMARY OF THE INVENTION

The present invention relates to the use of a growth factor bound to modified hyaluronic acid (HA)-based hydrogel particles (HGPs) for enhancing chondrogenesis in a subject in need thereof, and related medicaments.

A method for enhancing chondrogenesis in a subject in need thereof is provided. The method comprises administering to the subject an effective amount of a pharmaceutical composition comprising a growth factor bound to hyaluronic acid (HA)-based hydrogel particles (HGPs). The hyaluronic acid (HA)-based hydrogel particles (HGPs) are conjugated with a heparan sulfate proteoglycan (HSPG), preferably a bioactive domain of a HSPG. The pharmaceutical composition may be administered to the subject by injection.

The HSPG may comprise perlecan or a functional fragment or variant thereof. Preferably, the HSPG comprises perlecan domain 1 (PlnD1). The HSPG may comprise an amino acid sequence selected from SEQ ID NO: 1-5, preferably SEQ ID NO: 1.

The growth factor may be a heparan sulfate binding growth factor (HBGF). The HBGF may be bone morphogenetic protein 2 (BMP2). The growth factor may be released from the HA-based HGPs in the subject after the administration. For example, the growth factor may be released at least 7 or 14 days, preferably at least 7 days, after the administration.

In the method according to the present invention, the number of chondrocytes and/or cartilage synthesis may increase in the subject after the administration.

The subject may be an animal, preferably a mammal, more preferably a human.

In some embodiments, the subject may have suffered cartilage damage. The cartilage damage in the subject may be improved after the administration. The improvement may occur at least 7 or 14 days, preferably at least 7 days, after the administration.

In other embodiments, the subject may have suffered osteoarthritis (OA). The OA in the subject may be improved after the administration. The improvement may occur at least 7 or 14 days, preferably at least 7 days, after the administration.

In yet other embodiments, the subject may be predisposed to cartilage damage. The cartilage damage may be prevented in the subject after the administration. The prevention may occur at least 7 or 14 days, preferably at least 7 days, after the administration.

According to the present invention, the level of an extracellular matrix (ECM) protein and/or the expression of a cartilage synthesis gene in the subject may be increased after the administration. The increase may occur at least 7 or 14 days, preferably at least 7 days, after the administration. The cartilage synthesis gene may be selected from the group consisting of type II collagen, proteoglycan (e.g., aggrecan, perlecan, and type IX collagen), xylosyltransferase, cartilage oligomeric matrix protein (COMP), and exostosin (e.g., EXT1 and 2) genes.

According to the present invention, the expression of a cartilage degrading enzyme gene in the subject may be decreased after the administration, and/or the expression of the α1 chain of type X collagen (Col10α1) gene may be decreased after the administration. The cartilage degrading enzyme gene may be selected from the group consisting of Mmp3, Mmp13, Adamts5 and proinflammatory cytokine (e.g., IL1β and TNFα) genes.

In the method according to the present invention, the pharmaceutical composition may further comprise a bioactive compound. The bioactive compound may be selected from the group consisting of antifibrotic drugs, cell adhesive molecules, cytokines and non steroid anti-inflammatory drugs (NSAIDs) (e.g., Cox-2).

BRIEF DESCRIPTION OF THE DRAWINGS

FIG. 1 shows the amino acid sequence of perlecan domain 1 (PlnD1) from (A) human (SEQ ID NO: 1, amino acids 22-193, GenBank Accession No. NP_005520), (B) mouse (SEQ ID NO: 2, amino acids 22-194, GenBank Accession No. NP_032331), (C) cow (SEQ ID NO: 3, amino acids 12-183, GenBank Accession No. DAA32243), (D) rabbit (SEQ ID NO: 4, amino acids 68-239, GenBank Accession No. XP_002716087), and (E) chicken (SEQ ID NO: 5, amino acids 28-193, GenBank Accession No. NP_001001876).

DETAILED DESCRIPTION OF THE INVENTION

Figure 2:
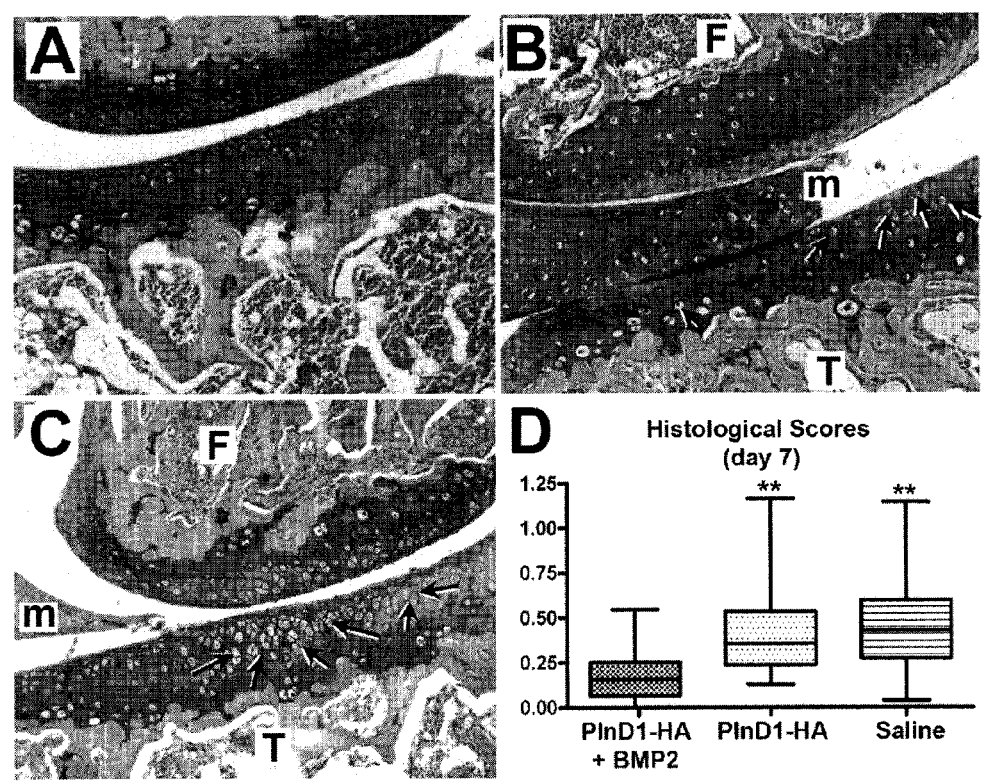
FIG. 2 shows (A-C) histological sections of papain-damaged mouse knees processed 7 days post repair or control treatments and stained with Safranin-O and Fast Green and (D) histological scores of cartilage damages. Knees treated with PlnD1-HA/BMP2 showed a normal smooth articular cartilage appearance (A) and had significantly less OA damage than the knees treated with either saline (B) or PlnD1-HA (C), which displayed proteoglycan depletion as indicated by a loss of Safranin-O staining as well as small fibrillations. Chondrocyte clusters are indicated by arrows in articular cartilage of both saline and PlnD1-HA-treated papain-damaged knees (B and C). Box and whiskers plot in panel D shows the median (central line), 75 percentile (boxes) and the entire range of scores obtained seven days after treatment of papain-damaged knees (n=5 for control injected twice with saline; n=9 for all the other groups). ** indicates p<0.001 when compared to PlnD1-HA/BMP2. No statistical difference is seen between the scores obtained in control knees injected with saline twice and the papain-injected knees treated with BMP2-loaded PlnD10HA particles (p=0.824). T, tibia; F, femur; m, meniscus.

The present invention is based on the discovery of a growth factor delivery system that potentiates the anabolic activity of the growth factor (e.g., BMP2) in a subject.

The terms "protein" and "polypeptide" are used herein interchangeably, and refer to a polymer of amino acid residues with no limitation with respect to the minimum length of the polymer. Preferably, the protein or polypeptide has at least 20 amino acids. The definition includes full-length proteins and fragments thereof, as well as modifications thereof (e.g., glycosylation, phosphorylation, deletions, additions and substitutions). A "functional fragment" of a protein refers to a fragment of the protein that retains the same function as the protein.

The term "variant" of a protein used herein refers to a polypeptide having an amino acid sequence that is the same as that of the protein except having at least one amino acid modified, for example, deleted, inserted, or replaced, respectively. The amino acid replacement may be a conservative amino acid substitution, preferably at a non-essential amino acid residue in the protein. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A variant of a protein may have an amino acid sequence at least about 80%, 90%, 95%, or 99%, preferably at least about 90%, more preferably at least about 95%, identical to the amino acid sequence of the protein. Preferably, a variant is a functional variant of a protein that retains the same function as the protein.

The term "derived from" used herein refers to an origin or source, and may include naturally occurring, recombinant, unpurified or purified molecules. A protein or polypeptide derived from an original protein or polypeptide may be a fragment or variant of the original protein or polypeptide.

The term "biomaterial" used herein refers to any synthetic, artificial, or natural materials biocompatible for use in a subject. It may comprise a tissue artificially engineered by recombinant techniques known in the art.

The present invention provides various methods, including a method for enhancing chondrogenesis in a subject in need thereof, a method for increasing or promoting cartilage synthesis in a subject in need thereof, and a method for treating, slowing, or preventing cartilage damage in a subject in need thereof. These methods comprise administering to the subject an effective amount of a pharmaceutical composition comprising a growth factor bound to hyaluronic acid (HA)-based hydrogel particles (HGPs), which are conjugated with a bioactive portion or the full length heparan sulfate proteoglycan (HSPG).

The term "chondrogenesis" used herein refers to the process by which cartilage is developed. The cartilage may be located in many areas in an animal body, for example, a joint, a rib cage, an ear, a nose, an elbow, a knee, a hip, a digit, a wrist, an ankle or an intervertebral disc. The cartilage may be elastic cartilage, hyaline cartilage or fibrocartilage.

The term "enhancing chondrogenesis" used herein refers to increasing or promoting the level of cartilage development or synthesis. The level of chondrogenesis (i.e., cartilage development or cartilage synthesis) may be determined by conventional tests or assays known in the art. For example, glycosaminoglycan synthesis may be visualized by dyes with high affinity for polyanions such as alcian blue or safraninO and/or quantified using the 1,9-dimethyl methylene blue (DMMB) method. For example, the enhancement of chondrogenesis may be evidenced by an increase in the number of chondrocytes, an increase in articular cartilage ECM components, an increase in the expression level of a cartilage synthesis marker, a decrease in the expression level of a cartilage degrading enzyme, hypertrophy marker, or the appearance of a chondroitin sulfate 846 (CS 846, marker of aggrecan synthesis) neoepitope. Cartilage ECM components include aggrecan and minor proteoglycans such as perlecan, biglycan and decorin, type II and minor collagens such as type IX and XVI, non collagenous proteins such as cartilage oligomeric protein (COMP) and cartilage link protein (HAPLN1). A cartilage synthesis marker may be any gene product that facilitates or improves chondrogenesis, for example, type II, type IX collagens, aggrecan, perlecan, cartilage non-collagenous proteins, and enzymes involved in glycosaminoglycan synthesis (e.g., xylosyltransferase, exostosins, etc.). A proteoglycan is a protein that is heavily glycosylated. For example, the proteoglycan may be selected from the group consisting of aggrecan, perlecan, and type IX collagen. A cartilage degradation enzyme is an enzyme that limits or prevents chondrogenesis, or promotes cartilage degradation. For example, the cartilage degradation enzyme may be Mmp3, Mmp13, Adamts5. Metalloproteinase-generated neoepitopes can also be used as markers of degradation. A hypertrophy marker may be $\alpha 1$ chain of type X collagen (Col10$\alpha$1), or Mmp13, transglutaminase 2 (TG2) and may be associated with ectopic calcification/biomineralization.

A subject may be an animal, including a mammal, for example, a human, a mouse, a cow, a horse, a chicken, a dog, a cat, and a rabbit. The animal may be an agricultural animal (e.g., horse, cow and chicken) or a pet (e.g., dog and cat). The subject is preferably a human or a mouse, more preferably a human. The subject may be a male or female. The subject may also be a newborn, child or adult. The subject may have suffered or predisposed to a disease or medical condition. Exemplary diseases and medical conditions include cartilage damage, joint damage, osteoarthritis (OA), and chondrodysplasias. The OA may be caused by joint damage, trauma, aging or congenital defect or mutation.

A heparan sulfate proteoglycan (HSPG) is a proteoglycan having one or more heparan sulfate (HS) chains attached to a protein, preferably an ECM protein. The HSPG may comprise an ECM protein, for example, perlecan, agrin, type IX collagens, syndecans and glypicans, or a functional fragment or variant thereof. Preferably, the HSPG comprises perlecan or a function fragment or variant thereof. More preferably, the HSPG comprises perlecan domain 1 (PlnD1) or a function fragment or variant thereof.

The HSPG may have a size of less than about 500 kDa, preferably less than about 200 kDa, more preferably less than about 100 kDa, most preferably less than about 25 kDa.

The HSPG may be obtained in various ways known in the art. For example, the HSPG may be a naturally occurring HSPG purified from a biological sample (e.g., a cell, a tissue or an organ), or an artificial HSPG produced recombinantly or synthesized chemically.

The HSPG may be derived from any mammal, for example, a human, a mouse, a cow, a rabbit or a chicken, preferably a human and a mouse, more preferably a human. The HSPG may comprise an amino acid sequence of a naturally occurring protein or a functional fragment or variant thereof. Preferably, naturally occurring protein is perlecan. The gene sequences and protein sequences of perlecan and its PlnD1 in various mammals are known, for example, PlnD1 amino acid sequences from human (SEQ ID NO: 1), mouse (SEQ ID NO: 2), cow (SEQ ID NO: 3), rabbit (SEQ ID NO: 4) and chicken (SEQ ID NO: 5) (FIG. 1).

The term "growth factor" used herein refers to a substance capable of stimulating or promoting cellular growth, proliferation and/or cellular differentiation. It may be a protein or a steroid hormone, either naturally occurring or artificially synthesized. The growth factor is preferably a growth factor that enhances chondrogenesis, or promotes growth and proliferation of cells such as bone cells and cartilage cells. Examples of the growth factors include hedgehog proteins, transforming growth factors-$\beta$ (TGF-$\beta$ super-family members including bone morphogenetic proteins (BMPs), fibroblast growth factors (FGF), platelet derived growth factors (PDGF), vascular endothelial growth factors (VEGF), heparin-binding epidermal growth factor (HB-EGF), CCN family members including connective tissue growth factor (CTGF), hepatocyte growth factor (HGF), Wnts, Midkine, and Pleiotrophin. The growth factor may be a heparan sulfate binding growth factor (HBGF), for example, BMP2, TGF-β1, FGF2, VEGF, hepatocyte growth factor (HGF), connective tissue growth factor (CTGF), HB-EGF, Wnts, Midkine, and Pleiotrophin, preferably BMP2, FGF2 and HGF, more preferably BMP2. The pharmaceutical composition may comprise about 0.001-1000, 0.05-100, 0.1-10, 0.5-2.0, 0.65-1.6, or 0.75-1.5 µg/ml of the growth factor.

Hyaluronic acid (HA)-based hydrogel particles (HGPs) are microgels. They may be prepared using conventional chemical techniques (e.g., inverse emulsion polymerization technique) to control size, improve enzymatic stability, and define surface functionality. See Jha et al., Perlecan domain I-conjugated, hyaluronic acid-based hydrogel particles for enhanced chondrogenic differentiation via BMP-2 release, *Biomaterials* 2009;30:6964-6975. The HA-based HGPs are conjugated with a bioactive portion or the full length of the HSPG. The growth factor is bound to the HA-based HGPs, preferably via the HSPG. The pharmaceutical composition may comprise about 0.01-1000, 0.1-100, 1-10, 4.5-7.5, 5-7, or 5.9-6.1 mg/ml of HA-based HGPs.

The term "an effective amount" refers to an amount of a pharmaceutical composition comprising a growth factor (e.g., BMP2) bound to HA-based HGPs conjugated to a HSPG module (e.g., PlnD1) required to achieve a stated goal (e.g., enhancing chondrogenesis, increasing or promoting cartilage synthesis, and/or treating or preventing cartilage damage in a subject in need thereof). The effective amount of a pharmaceutical composition comprising a growth factor bounded to HA-based HGPs conjugated to a HSPG may vary depending upon the stated goal, the physical characteristics of the subject, the nature and severity of the cartilage damage, existence of related or unrelated medical conditions, the nature of the growth factor, the HA-based HGPs and/or HSPG, the composition comprising the growth factor (e.g., BMPs), the means of administering the drug to the subject, and the administration route. A specific dose for a given subject may generally be set by the judgment of a physician. The pharmaceutical composition may be administered to the subject in one or multiple doses.

The pharmaceutical composition may further comprise a pharmaceutically acceptable carrier or diluent. Suitable carriers, diluent and other excipients are well known in the art.

The pharmaceutical composition may be administered to the subject over a period of hours, days, weeks or months. It may also be administered once, twice, thrice or more times a day, once every two days, once every three days, once every four days, once every five days, once every six days, once a week, once every 10 days, once every two weeks, once every three weeks, once a month, or even less frequently.

The pharmaceutical composition may be formulated, for example, for oral, sublingual, intranasal, intraocular, rectal, transdermal, mucosal, topical or parenteral administration. Parenteral administration may include intradermal, subcutaneous (s.c., s.q., sub-Q, Hypo), intra-articular (i.a.), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids) administration. Any device suitable for parenteral injection or infusion of the composition may be used for such administration. According to the present invention, the pharmaceutical composition is preferably administered to the subject by implantation or injection, more preferably by intra-articular injection, at, for example, where cartilage damage occurs or is suspected to occur.

In some embodiments, the growth factor is released from the HA-based HGPs in the subject after the administration. The growth factor may be released at least about 1, 2, 3, 4, 5, 6, 7, 8, 9, 10, 11, 12, 13, 14, 15, 20 or 30 days after the administration. Less than about 1, 5, 10, 20, 30, 40, 50, 60, 70, 80, or 90% of the growth factor bound to the HA-based HGPs may have been released from the HA-based HGPs about 1, 2, 3, 4, 5, 6, 7, 8, 9, 10, 11, 12, 13, 14, 15, 20 or 30 days after the administration.

In other embodiments, the number of chondrocytes increases in the subject after the administration. The increase may occur at least about 1, 2, 3, 4, 5, 6, 7, 8, 9, 10, 11, 12, 13, 14, 15, 20 or 30 days after the administration. Preferably, the increase occurs at where cartilage damage occurs or is suspected to occur in the subject.

In the methods according to the present invention, the subject may have suffered cartilage damage, joint damage, or OA, and the cartilage damage, joint damage, or OA may be improved after the administration. The improvement may occur at least about 1, 2, 3, 4, 5, 6, 7, 8, 9, 10, 11, 12, 13, 14, 15, 20 or 30 days after the administration.

In the methods according to the present invention, the subject may be predisposed to cartilage damage or OA, the cartilage damage or OA may be prevented after the administration. The prevention may occur at least about 1, 2, 3, 4, 5, 6, 7, 8, 9, 10, 11, 12, 13, 14, 15, 20 or 30 days after the administration.

According to the present invention, the subject may exhibit some changes in certain morphology or gene expression after the administration. For example, the cellularity at a superficial articular cartilage layer in the subject may be increased. The level of an ECM protein may be increased. The ECM protein may be a cartilage ECM protein such as perlecan, agrin, type II and IX collagens, syndecans and glypicans. The expression of a cartilage synthesis marker may be increased. A cartilage synthesis marker may be any gene product that facilitates or improves chondrogenesis, for example, type II, type IX collagens, aggrecan, perlecan, cartilage non-collagenous proteins, and enzymes involved in glycosaminoglycan synthesis (e.g., xylosyltransferase, exostosins, etc.). A proteoglycan is a protein that is heavily glycosylated. For example, the proteoglycan may be selected from the group consisting of aggrecan, perlecan, and type IX collagen. The expression of a cartilage degrading enzyme, proinflammatory cytokine (e.g., IL1) or a hypertrophy marker may be decreased. The cartilage degrading enzyme is an enzyme that limits or prevents chondrogenesis, or promotes cartilage degradation. For example, the cartilage degradation enzyme may be Mmp3, Mmp13, Adamts5 or a proinflammatory cytokine (e.g., IL1β and TNFα). Metalloproteinase-generated neoepitopes can also be used as markers of degradation. A hypertrophy marker may be α1 chain of type X collagen (Col10α1), or Mmp13, transglutaminase 2 (TG2) and its expression may be accompanied by ectopic calcification/biomineralization.

According the present invention, the method may further comprise administering to the subject a bioactive compound. The bioactive compound may be selected from the group consisting of antifibrotic drugs, non steroid anti-inflammatory drugs (NSAIDs), cell adhesive molecules and cytokines. Preferably, the bioactive compound is administered to the subject in an amount effective to enhance chondrogenesis or promoting cartilage synthesis in the subject. The bioactive compound may be administered in the same pharmaceutical composition comprising a growth factor bounded to HA-based HGPs conjugated to a HSPG.

For each method of the present invention, a medicament is provided. The medicament is useful for enhancing chondrogenesis in a subject in need thereof, for increasing or promoting cartilage synthesis in a subject in need thereof, and/or for treating or preventing cartilage damage in a subject in need thereof. The medicament comprises an effective amount of a pharmaceutical composition comprising a growth factor bound to hyaluronic acid (HA)-based hydrogel particles (HGPs), which are conjugated with a bioactive portion or the full length of a heparan sulfate proteoglycan (HSPG). The growth factor is preferably a heparan sulfate binding growth factor (HBGF), more preferably BMP2. The HSGP is preferably perlecan or a functional fragment or variant thereof, more preferably PlnD1. The medicament may comprise about 0.001-1000, 0.05-100, 0.1-10, 0.5-2.0, 0.65-1.6, or 0.75-1.5 µg/ml of the growth factor, and/or about 0.01-1000, 0.1-100, 1-10, 4.5-7.5, 5-7, or 5.9-6.1 mg/ml of the HA-based HGPs. The medicament may further comprise a pharmaceutically acceptable carrier or diluent. The medicament may further comprise a bioactive compound, for example, selected from the group consisting of antifibrotic drugs, NSAID, cell adhesive molecules and cytokines.

For each medicament of the present invention, a method for preparing the medicament is provided. The preparation method comprises admixing a growth factor with a pharmaceutically acceptable carrier or diluent. The growth factor is bound to HA-based HGPs, which are conjugated with a bioactive portion or the full length of a heparan sulfate proteoglycan (HSPG). The growth factor is preferably a heparan sulfate binding growth factor (HBGF), more preferably BMP2. The HSGP is preferably pelecan or a functional fragment or variant thereof, more preferably PlnD1. The resulting medicament may comprise about 0.001-1000, 0.05-100, 0.1-10, 0.5-2.0, 0.65-1.6, or 0.75-1.5 µg/ml of the growth factor, and/or about 0.01-1000, 0.1-100, 1-10, 4.5-7.5, 5-7, or 5.9-6.1 mg/ml of the HA-based HGPs. The method may further comprise admixing a bioactive compound, for example, selected from the group consisting of antifibrotic drugs, NSAIDs, cell adhesive molecules and cytokines.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

EXAMPLE 1

Perlecan Domain 1-Hyaluronan Based Microgels Prolong the Anabolic Effect of BMP2 in Mouse Articular Cartilage Objective: The goal of this study was to prolong the action of bone morphogenetic protein 2 (BMP2) in knee joint cavities to stimulate matrix synthesis by resident chondrocytes and promote cartilage healing.

Design: A module of perlecan (PlnD1) bearing heparan sulfate chains was covalently immobilized to hyaluronic acid (HA) microgels for the controlled release of BMP2 in vivo. Osteoarthritis (OA)-like damage induced by papain was treated by intra-articular injection of PlnD1-HA particles with BMP2 bound to HS. Control injections consisted of BMP2 free PlnD1-HA particles, HA particles, free BMP2 or saline. Knees dissected following these injections were analyzed using histological, immunostaining and gene expression approaches.

Results: After a healing period, knees treated with PlnD1-HA/BMP2 had lesser remaining OA-like damage compared to control knees. In addition, the PlnD1-HA/BMP2-treated knees had higher mRNA levels encoding for type II collagen, proteoglycans, and xylosyltransferase 1, a rate-limiting anabolic enzyme involved in the biosynthesis of glycosaminoglycan chains, relative to control knees. This finding was paralleled by enhanced levels of aggrecan in the articular cartilage of PlnD1-HA/BMP2 treated knees. Additionally, decreases in the mRNA levels encoding for cartilage-degrading enzymes and type X collagen were seen relative to controls.

Conclusions: PlnD1-HA microgels act as an efficient in vivo delivery system for BMP2 and the controlled or slow release of BMP2 has an overall anabolic effect on murine articular cartilage by stimulating the synthesis of proteoglycans and cartilage matrix. Ultimately, PlnD1-HA/BMP2 may serve as an injectable therapeutic agent for slowing or preventing the onset of irreversible OA after knee injury.

Method.

Preparation of PlnD1-HA Microgels

Recombinant human BMP2 (R&D Systems, Minneapolis, Minn.) stock was prepared at a concentration of 10 µg/ml in saline containing 4 mM HCl and 0.1% (w/v) mouse albumin (Innovative Research, Novi, Mich.). Recombinant mouse PlnD1 was expressed by stably transfected kidney cells and purified using an immunoaffinity chromatography approach following established protocols (Yang et al., 2005, *Tissue Eng.* 11:76-89; Costell et al., 1997, *Eur. J. Biochem.* 243: 115-21). Post-translational modification of PlnD1 by heparan sulfate (HS) was verified by observing a change in its electrophoretic mobility following heparinase I, II, and III and chondroitinase AC treatments. Because the absence of HS results in loss of BMP-2 binding activity only PlnD1 decorated by HS chains was used in this study. PlnD1-HA microgels were prepared as described by Jha et al. (*Biomaterials* 2009;30:6964-6975). Briefly, PlnDI was conjugated to HA microgels via the core protein through a polyethylene glycol (PEG) linker. The aldehyde groups in HA microgels were passivated by glycine and the residual hydrazide groups were allowed to react with a large excess of PEG dial dibutyraldehyde. The generated aldehyde groups were subsequently used for reaction with the lysine amine residues in the core protein. The PlnDI-conjugated HA particles were passivated again with glycine before being used for BMP-2 loading.

The need for PlnD1 bioconjugation to a HA carrier to increase in vivo retention in the articular knee cavity, was tested previously by injecting intra-articularly Alexa 568-labeled PlnD1. In vivo knee imaging showed that PlnD1 was clearly visible for 4-6 hours only when stabilized by a HA carrier. Bioconjugation of PlnD1 to HA was performed as described by Jha et al. (*Biomaterials* 2009;30:6964-6975). The presence of glycosaminoglycan modifications was controlled by staining the microgels with Alcian blue. Additionally, the selective binding capacity and release of BMP2 were measured using an ELISA assay as described by Jha et al. (*Biomaterials* 2009;30:6964-6975). Finally, PlnD1-HA microgel bioactivity was evaluated in vitro using a micromass culture system as described by Jha et al. (*Biomaterials* 2009;30:6964-6975). Once the PlnD1-HA microgels passed all these control quality tests, they were extensively rinsed in 70% (v/v) ethanol and saline, pelleted at 3,000 rpm and resuspended in sterile saline at a concentration of 6 mg/ml. Approximately 1 milligram of PlnD1-HA particles was combined with 250 ng of BMP2 freshly prepared as described above. Both PlnD1-HA control and PlnD1-HA/

BMP2 mixtures were preincubated for an hour at room temperature prior to performing the intra-articular injections.

Animals

Ten to eleven week-old male C57Bl/6J mice were used for the study. After surgery, mice were housed in individual cages and fed normal diet and tap water. Unless otherwise stated, nine animals were used per group per time point.

Intra-articular Injections

OA-like damage was induced by injecting intra-articularly 6 µl/knee of a 1% (w/v) papain solution prepared in a saline solution containing 5 mM L-Cysteine. After allowing 7 days for the OA-like damage to develop, the various test treatments were administered via intra-articular injection and the knees were allowed to heal for 7 or 14 days, after which the efficiency of each treatment condition to counteract the OA-like damage was evaluated after the animals were sacrificed. In the initial study, the usefulness of PlnD1-HA particles plus BMP2 to limit joint damage was compared with control growth factor-free PlnD1-HA particles or saline. In subsequent studies, HA particles alone or BMP2 alone served as additional control groups, and the knees were dissected 7 days after the treatment injections. To assess whether transcriptional changes are early and precede/parallel repair, RNA were extracted at day 1 and day 7 following treatment injection with PlnD1-HA plus BMP2 or PlnD1-HA control microgels (see below).

Histological Scoring

Knees were fixed in 10% (v/v) formalin and decalcified in a 10% (v/v) formic acid solution prepared in 1×PBS and replaced daily for 7 days. Following decalcification, the knees were paraffin-embedded and the entire block was sectioned to obtain 6 µm-thick frontal sections. After deparaffinization, the sections were either stained histologically using a standard Safranin O and Fast Green staining procedure or immunostained (see below). Scoring was done in the four compartments of the knee: Medial Tibia (MT), Medial Femur (MF), Lateral Tibia (LT) and Lateral Femur (LF) using the modified semi-quantitative scoring scale as described in by Glasson. Briefly, the scores attributed in this study are: score 0=normal cartilage, score 0.5=loss of Safranin O staining with a normal articular surface, score 1=small fibrillations or roughened articular surface, and score 2=fibrillations extending into the superficial lamina. For each knee analyzed, 12-15 slides encompassing the entire joint were blinded and scored by two independent observers. Mean scores were calculated for each compartment of the knee. The histological scores obtained at days 7 and 14 after the treatment injections were analyzed using Kruskal-Wallis test. Bonferroni correction was performed for multiple comparisons and p values less than 0.01 were considered significant.

Immunohistochemistry

Knee sections obtained as described above were deparaffinized with xylene and dehydrated with 100% and 70% ethanol. Antigen retrieval was performed with Dako (Carpinteria, Calif.) antigen retrieval solution for 1 hour and then washed with 1×PBS. The sections were blocked overnight with 3% (w/v) BSA and 2% (v/v) goat serum. Primary antibody [rabbit anti-mouse aggrecan (Chemicon International Inc., Temecula, Calif.) or rabbit anti-mouse collagen II (Biodesign International, Saco, Me.)] was incubated with the tissue section for 4 hours at 37° C. After washing in PBS, Alexa 488 conjugated goat anti-rabbit secondary antibody (Invitrogen, Carlsbad, Calif.) at 1 to 200 dilution and DRAQ5™ (Biostatus, Leicestershire, United Kingdom) at a 1 to 1000 dilution were incubated at 37° C. for 1 hour. Following washes in PBS, sections were mounted with anti-fading agent and viewed under a Zeiss LSM confocal microscope.

Quantitative Real-Time PCR (Q-PCR)

To examine transcriptional changes in cartilage-specific marker expression, mRNA was extracted from both tibiae and femora of 3-4 papain-damaged knees treated with either PlnD1-HA/BMP2 (combined treatment) or PlnD1-HA (carrier only control) microgels. Tissue softening and mild decalcification were induced in 0.5M EDTA (Sigma-Aldrich, St. Louis, Mo.) on a rocking platform overnight at 4° C. RNA extraction was performed using the RNeasy® fibrous tissue mini kit (Qiagen, Valencia, Calif.) and incubated for 1 hour with DNAase (Turbo DNA-free, Ambion Inc, Austin, Tex.). One microgram of mRNA was used as a template to synthesize cDNA in 20 µl reverse transcription PCR reaction with the iScript™ cDNA synthesis kit (Bio-Rad, Hercules, Calif.) according to the manufacturers' instructions. Quantitative PCR (Q-PCR) was performed as follows: 5 µl of primer mix (10 mM concentration each primer), 12.5 µl of SYBR® green PCR master mix (SA Biosciences, Frederick, Md.), 6.5 µl of water and 1 µl of cDNA. The Q-PCR was run in triplicate using the ABI PRISM® 7000 Sequence Detector System (AB Applied Biosystems, Life Technologies, Carlsbad, Calif.) under the following cycling conditions: 2 min at 50° C., 10 min at 95° C. followed by 40 cycles of 15 sec at 95° C. and 1 min at 60° C. Primer sets specific for cartilage markers were purchased from SA Biosciences (Frederick, Md.) and included type II and X collagens (Col2α1 and Col10α1); aggrecan (Acan); perlecan (Hspg2), the major HSPG produced in the pericellular matrix of chondrocytes; and xylosyltransferase 1 (Xylt1), the isoform of found in cartilage. In addition, primers were purchased for enzymes whose levels increase during OA: 1) two aggrecan degrading enzymes, matrix metalloproteinase 3 (Mmp3) and aggrecanase-2 (Adamts5), and 2) one enzyme primarily responsible for type II collagen breakdown (Mmp13). The cycle threshold (CT) values for each gene of interest were corrected with that of GAPDH and the relative fold change in the mRNA expression was calculated using the $2^{-\Delta\Delta CT}$ formula as described. The experiment was performed in triplicate (total of 9-12 knees/condition) and the mean fold change of the relative mRNA levels in knees treated with PlnD1-HA/BMP2 (combined treatment) was compared to knees injected with PlnD1-HA microparticles (carrier only control) either 1 or 7 days following treatment.

Results.

Effect of BMP2-loaded PlnD1-HA Microparticles on Damaged Articular Cartilage in Mice.

The efficacy of the various treatments in counteracting the damages produced by papain was evaluated by histological scoring (FIG. 2D). After 7 days, PlnD1-HA/BMP2 treated knees had significantly lesser OA-like damage than the knees treated with PlnD1-HA (p=$10^{-5}$, FIG. 2D) or the knees treated with saline (p=$10^{-5}$, FIG. 2D). All coronal knee sections obtained 7 days after a single injection of PlnD1-HA/BMP2 microgels showed a smooth and thick articular cartilage surface with numerous chondrocytic clusters of normal appearance surrounded by intense Safranin-O staining, suggesting that PlnDI-HA/BMP2 enhanced chondrogenic activity of resident articular chondrocytes by stimulating synthesis of proteoglycans (FIG. 2A). This result was seen in around 90% of the animals tested (8 out of 9 injected knees).

Figure 3:
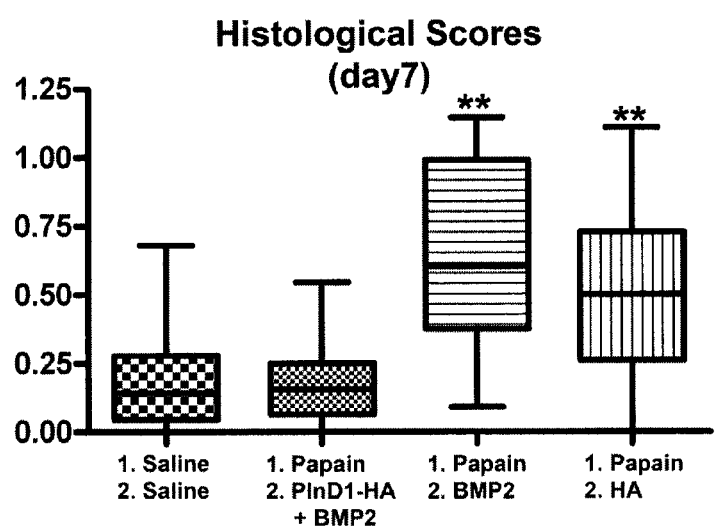
FIG. 3 is a box and whisker plot showing the median (central line), 25-75 percentile (boxes) and the entire range of scores obtained 7 days after treatment of saline or papain-damaged knees (n=4 for control saline; n=9 for the three other groups). ** indicates p<0.001 when compared to PlnD1-HA/BMP2. No statistical difference is seen between the scores obtained in control knees injected with saline twice and the papain-injected knees treated with BMP2-loaded PlnD1-HA particles.

In contrast, saline and PlnD1-HA-injected knees demonstrated obvious proteoglycan depletion and small fibrillations in approximately 80% (7/9 knees) and 70% (6/9 knees) of the individuals tested, respectively (FIG. 2B-C). In most of these affected knees the presence of chondrocyte clusters was visible near the joint surface in the eroding proteoglycan-depleted region (see arrows in FIG. 2B-C). In addition, albeit slightly lower scores were obtained following injection with PlnD1-HA when compared with saline, there was no statistical difference between the histological scores for these two conditions (p=0.299, FIG. 2D). Additional control treatments consisting of a single injection of either BMP2 or HA microgels in the absence of PlnD1 did not reverse proteoglycan loss (FIG. 3). More importantly, the morphology of papain-damaged knees treated with BMP2-loaded PlnD1-HA particles was not distinguishable from knees that were injected twice with a control saline solution in place of papain and the day 7 treatment (FIG. 3). Papain-damaged knees treated with free unbound BMP-2 had a significantly higher OA score compared to knees treated with PlnD1-HA/BMP2 indicating the lack of chondrogenic/repair activity. Additionally, the OA score obtained following BMP2 direct injection was not significantly different from scores obtained under other post-papain control injections: PlnD1-HA, HA, and saline (FIGS. 2D and 3).

Effect of PlnD1-HA/BMP2 particles on Articular Cartilage Transcript Levels

Cartilage Synthesis Markers

Figure 4:
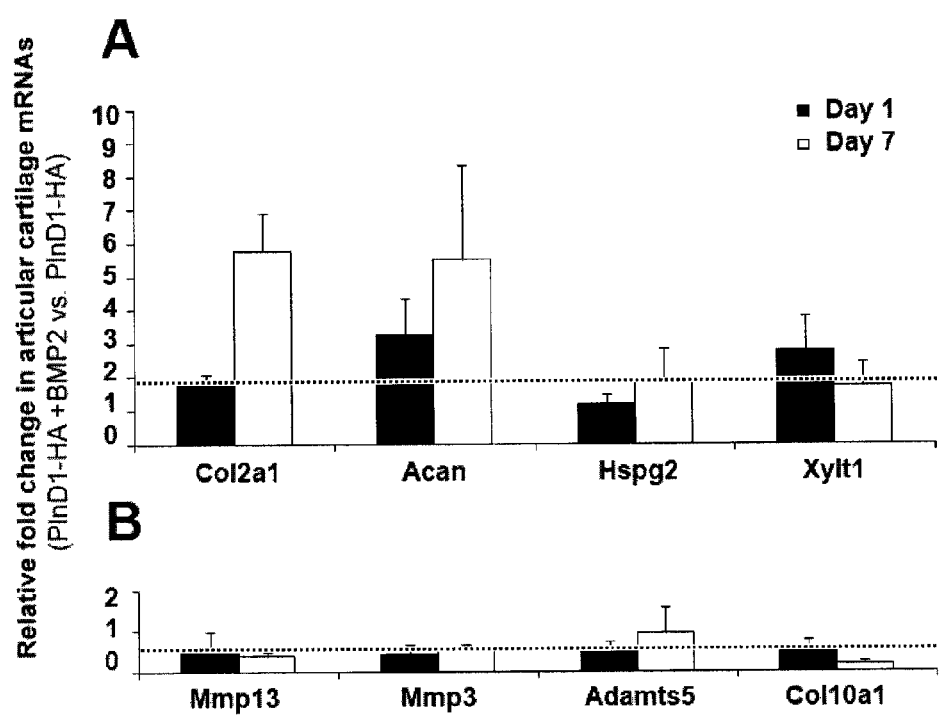
FIG. 4 shows the effect of the combined administration of BMP2 and PlnD1-HA particles on mRNA levels of articular cartilage ECM components and ECM-modifying enzymes. Fold changes in mRNA levels are shown for knees treated with BMP2-loaded PlnD1-HA particles relative to knees treated with growth factor free particles (control PlnD1-HA) on days 1 and 7 following intra-articular injections. (A) mRNA levels of the α1 chain of type II collagen (Col2α1), aggrecan (Acan), perlecan (Hspg2) and xylosyltransferase 1 (Xylt1) were significantly increased in knees treated with PlnD1-HA/BMP2 compared with control (PlnD1-HA) knees whereas (B) the opposite was seen with matrix degrading enzymes (Mmp 13, Mmp3, and Adamts5) and the α1 chain of type X collagen (Col10α1). Each fold change value equal or higher to 2 (above the dashed line in A) and equal or lower to 0.5 (below the dashed line in B) is considered statistically significant, when PlnD1-HA/BMP2 is compared with control PlnD1HA. Error bars represent standard deviations.

Transcripts levels of ECM components were measured in articular cartilage of papain damaged knees treated with either PlnD1-HA/BMP2 or growth factor free control PlnD1-HA particles (FIG. 4A). As early as one day post-treatment, the mRNA level for the α1 chain of the major fibrillar component of cartilage, type II collagen (Col2α1), was slightly, but significantly, increased 2-fold in cartilage extracted from knees treated with PlnD1-HA/BMP2 relative to control knees. This positive effect of PlnD1-HA/BMP2 particles continued with time and an almost 6-fold increase in the mRNA level of type II collagen of PlnD1-HA/BMP2 treated knees was seen at day 7 post-treatment when compared to control samples.

Transcript levels of the major cartilage proteoglycan, aggrecan, were 3-fold greater in PlnD1-HA/BMP2 knees than control knees at day 1 and about 5-fold greater than control knees at day 7. The mRNA levels of perlecan itself, the most abundant HSPG present in cartilage, were examined. The relative mRNA level of perlecan was significantly higher in the PlnD1-HA/BMP2 treated knees than the control knees at day 7. The relative levels of transcripts encoding for the enzyme that initiates glycoaminoglycan chain extension by adding the first sugar group to proteoglycans, xylosyltransferase 1 (Xylt1) also was measured. PlnD1-HA/BMP2 treated knees demonstrated a pronounced increase in mRNA encoding this enzyme primarily in the early post-treatment phase (day 1). The increase remained significant, albeit weaker, at day 7 when compared to control knees.

Cartilage Degradative Enzymes and Marker of Hypertrophy

The mRNA levels of degrading enzymes responsible for the breakdown of cartilage ECM components and type X collagen, a marker for chondrocyte hypertrophy and pathological calcification of articular cartilage were measured (FIG. 4B). The mRNA levels of both Mmp3 and Mmp13 were decreased significantly in the knees treated with PlnD1-HA/BMP2 compared to the control knees at day 1 and day 7 after treatment injections. The mRNA levels of Adamts5 were decreased at day 1 with no significant difference at day 7 between the PlnD1-HA/BMP2 treated and control knees. The level of transcripts encoding for the α1 chain of type X collagen, was significantly decreased by nearly five-fold at day 7 in PlnD1-HA/BMP2 treated vs. PlnD1-HA injected knees.

Comparative Analysis of ECM Protein Distribution in PlnD1-HA/BMP2 Treated Knees

Type II Collagen Immunoreactivity

Potential changes in the expression pattern of the major fibrillar component, type II collagen, was assessed by comparing immunostained sections of papain-damaged knee sections harvested 7 days after treatment with either BMP2-loaded PlnD1-HA particles or saline. There was no obvious difference in the intensity of the immune signal between knee sections treated with PlnD1-HA/BMP2 and control knee sections treated with saline or growth factor free control PlnD1-HA particles. Thus, the already strong fluorescent signal corresponding to type II collagen remained unchanged between these conditions (data not shown). One noticeable change upon administration of PlnD1-HA/BMP2 particles, however, was a consistent increase in the cellularity in the superficial articular cartilage layer when compared to control conditions and a concomitant increase in the overall extent of collagen type II-positive tissue.

Aggrecan Immunoreactivity

To correlate the higher levels of aggrecan transcripts in PlnD1-HA/BMP2-treated articular cartilage with corresponding protein expression, immunolabeling of treated knees was performed with an antibody directed against the aggrecan molecule using an indirect immunofluorescence approach (data not shown). The articular cartilage of knees treated with PlnD1-HA/BMP2 showed higher expression of aggrecan than control knees treated with PlnD1-HA or saline. In contrast, aggrecan signal in growth plate cartilage remained unchanged among all three experimental conditions and was used a positive control for antibody immunoreactivity.

PlnD1-HA Microgels Prolong BMP2 Cartilage Repair Activity In Vivo

Figure 5:
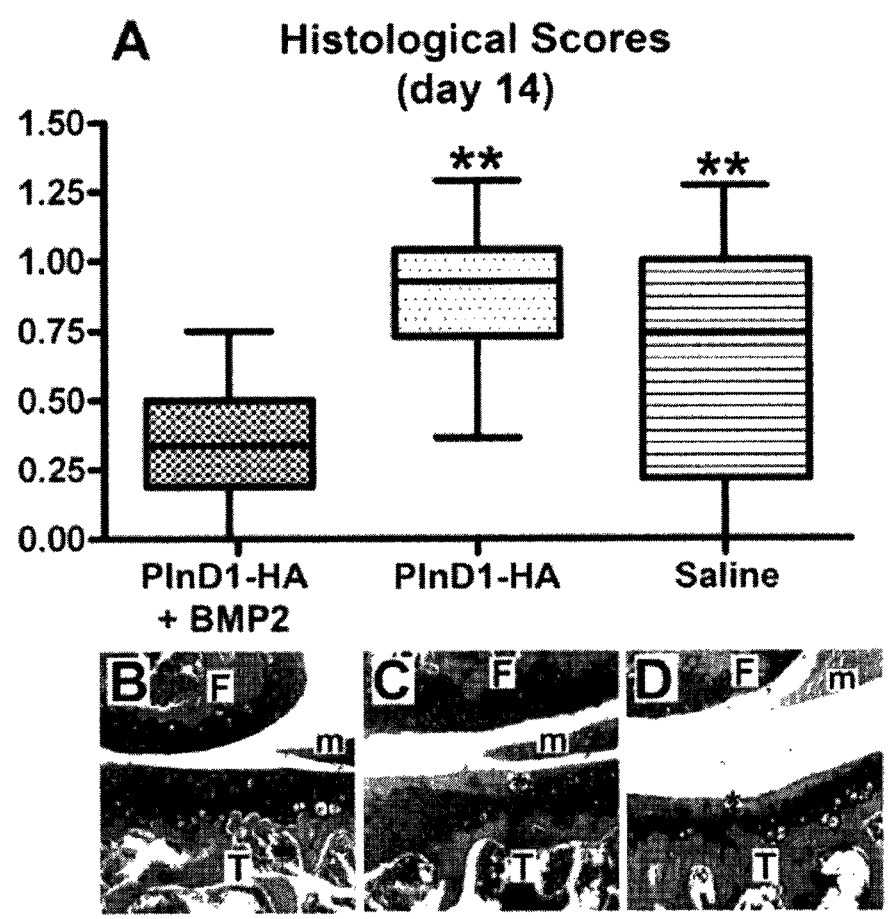
FIG. 5 shows (A) a box and whisker plot showing the median (central line), 25 to 75 percentile (boxes) and the entire range of scores obtained 14 days after treatment of papain-damaged knees (n=9 for each group), and (B-D) representative histological sections from papain-damaged mouse knees processed 7 days post repair (B, PlnD1-HA/BMP2) or control (C, PlnD1-HA; D, saline) treatments and stained with Safranin-O and Fast Green. ** indicates p<0.001 when compared to PlnD1-HA/BMP2. Proteoglycan depletion in the superficial articular cartilage layer is marked by an asterisk. F, femur; T, Tibia; m, meniscus.

To determine if PlnD1-HA microparticles can prolong the chondrogenic effect of BMP2 on articular cartilage over a longer period of time, the histological appearance of papain-damaged knees dissected 14 days was compared after a single intra-articular injection of either PlnD1-HA/BMP2, PlnD1-HA, or saline. The analysis of the histological scores showed that PlnD1-HA/BMP2-treated knees had lesser OA-like damage than the knees of the two control (PlnD1-HA and saline) groups (FIG. 5A). Although PlnD1-HA/BMP2 and PlnD1-HA treatments significantly increased between day 7 and day 14, these scores followed the same trends as the scores obtained after 7 days of treatment and PlnD1-HA/BMP2 treated knees at day 14 still displayed significantly less damage than knees treated with either PlnD1-HA or saline (p≤0.001 and p=0.005, respectively).

Discussion.

Despite its established anabolic effect during both chondrogenesis and the pathogenesis of OA, BMP2 usefulness in cartilage repair has been limited due to its short in vivo half life and induced side effects when administered at high doses. Indeed, when injected under its soluble form into the knee cavity it is rapidly cleared away through systemic passive diffusion/clearance, and/or inhibition through specific BMP antagonists and proteases. Additionally, burst induction from repetitive high dose injections or sustained overexpression through adenoviral genetic insertion of TGFβ family members are known to result in adverse side effects on adjacent joint tissues including induction of an inflammatory response, synovial fibrosis, and formation of de novo osteophytes at sites of tendon insertions or periosteal joint margins.

Consistent with previous reports, the single administration of soluble BMP2 in the current study neither induced side effects (expansion of the synovial membrane/subchondral bone sclerosis/osteophyte formation etc.) nor enhanced cartilage repair. For this reason, PlnD1 bearing HS chains was bioconjugated to a biocompatible carrier (HA microgel) to potentiate/prolong BMP2 action after injection in mouse knee cavities. Binding of BMP2 to HS chains with a native sulfation pattern serves two roles as it both protects BMP2 from being degraded and enhances its functional binding with cellular receptors through the formation of functional ternary complexes in which BMP2 interacts with both HS motifs and the BMP receptor complex. This form of non-covalent highly specific binding is important in retaining the growth factor bioactivity which could easily be compromised through covalent chemical bonds. Indeed, injection of BMP2 in combination with PlnD1-HA microgels in papain-damaged knees significantly improved histological scores when compared to all other treatments including free BMP2.

The significantly lesser OA damage observed in the PlnD1-HA/BMP2-treated knees extends previous in vitro findings that PlnD1-HA potentiates BMP2 and helps in spatial and temporal presentation of BMP2. Interestingly, scores obtained with PlnD1-HA microparticles in the absence of BMP2 were slightly improved relative to control saline injections. Although articular cartilage integrity obtained with PlnD1-HA particles remains significantly inferior to the one seen with BMP2-loaded particles, this observation suggests that carrier microparticles may have a small regenerative capacity themselves, perhaps by trapping endogenous BMP2 or other HS binding factors. Thus, it can be speculated that the release kinetics of BMP2 from PlnD1-HA microparticles are governed by the equilibrium between the free BMP2 released from the degrading cartilage matrix and those bound to the PlnD1-HA particles. Such dynamic model would support stimulation of repair pathways and prevention of interaction between active BMP2 molecules and their natural antagonists. Although this idea requires further investigation, it is clear from the data that the PlnD1-coupled HA microgels themselves are not responsible for knee damage worsening and may even be chondroprotective.

Comparative analysis of mRNA levels in articular cartilage following treatment with PlnD1-HA microgels in the presence or absence of BMP2 indicates that BMP2 release from these biomaterials rapidly increases the relative level of transcripts encoding for both aggrecan and its modifying enzyme (Xylt1) during cartilage repair processes. These initial transcriptional events soon were followed by a significant increase in the relative levels of both type II collagen and perlecan mRNAs. The fact that mRNA encoding for ECM components all were increased when BMP-2 was efficiently delivered through PlnD1-HA microgels strongly implies that the repair mechanisms involved under the experimental conditions primarily consist of de novo synthesis of cartilage matrix. In addition, the small but significant decrease of the relative mRNA levels encoding for Mmp3 and Mmp13 upon PlnD1-HA/BMP2 treatment suggests that inhibition of degradative pathways may also be involved in the stabilization of the articular cartilage matrix. This data contrasts with other reports in which BMP2 stable overexpression via adenoviral integration leads to an initial catabolic response by chondrocytes and boosts matrix turnover. The lack of catabolic effect under the condition indicates that controlled delivery of BMP2 induces a seemingly exclusive anabolic effect that may protect new and resident cartilage against further destruction. The significant and continuous increase in aggrecan transcript levels during the course of the experiment is accompanied by a transient transcriptional inhibition of Adamts5, the aggrecan-specific protease. Whereas up-regulation of Adamts5 gene expression is a well-accepted indicator of early disease progression, reestablishment of baseline levels (as seen at day 7 in the study) actually may be important for normal cartilage turnover and the creation of space for organized deposition of newly synthesized ECM components. Finally, reduction of both Mmp13 and type X collagen mRNA levels in treated versus control knees indicated that the global reparative effect of PlnD1-HA/BMP2 biomatrices on articular cartilage do not activate developmental program associated with cartilage growth plate terminal differentiation. Altogether, the gene expression data shows that BMP2 delivered through PlnD1-HA triggers both anabolic (by increasing the transcription of proteoglycans and type collagen) and protective responses (by lowering matrix degradation).

The replenishment of proteoglycans such as aggrecan with large negatively charged polysaccharide chains is essential for the restoration of the viscoelastic properties of normal functional hyaline cartilage with ability to resist compressive loads. Therefore, the aggrecan expression data strongly favors a reversion of the early OA damage induced by papain. In contrast, even though Col2α1 gene expression was significantly upregulated, type II collagen expression pattern remained unchanged among treatments. During early OA, the loss of aggrecan is initiated at the joint surface and progresses to the deeper zones before degradation of the collagen fibrillar meshwork. Similarly, the original collagen matrix might not have been destabilized under the experimental conditions and the lack of obvious change in type II collagen-specific signal among treatments is likely due to the difficulty of visualizing de novo expression above baseline levels. This idea is supported by the fact that the type II collagen triple helix is remarkably stable (half-life in cartilage ≥100 years).

In summary, it is demonstrated that single injection of BMP2 complexed to PlnD1/HA-based microgels in papain-damaged knees can increase the mRNA levels encoding articular cartilage matrix components, reverse proteoglycan loss and cartilage erosion, and inhibit cartilage degradative pathways and hypertrophy. Importantly, the data shows that BMP2 only promotes a strong and sustained anabolic response on compromised cartilage when administered in a physiologically-relevant form. Thus, covalent modification of HA with bioactive molecular complexes of native cartilage constitutes a new promising therapeutic option to control the anabolic response of articular cartilage chondrocytes and slow degradative processes in patients susceptible to develop OA at relatively young age. Problems associated with knee injury in young patients exposed to intense daily activities (athletes, military trainees, etc.) include the formation of fibrocartilage at sites of injury followed by progressive degeneration and development of severe OA. Future studies will investigate if multiple injections (weekly intra-articular injections over a period of at least 1.5 months during the acute degradative phase preceding full-thickness articular cartilage damage) of BMP2-releasing PlnD1-HA microgels can help preserve the normal structure of hyaline cartilage and slow disease progression in more severe instability-induced models of knee OA. Yet, recent recommendations for the use of preclinical models in the study and treatment of OA pointed out that less severe animal models (such as papain) are required to better evaluate potential therapies for use in human OA as overly severe experimental models (surgical knee destabilization, iodoacetate intra-articular knee injections) may only constitute tools to study mechanisms involved in irreversible disease progression. In conclusion, the current study shows for the first time that the PlnD1-conjugated, HA-based microgels can enhance BMP2 bioactivity in vivo and are promising injectable materials for the targeted delivery of HBGFs without the initiation of side effects often seen following repetitive administration of growth factors.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for enhancing cartilage repair in a subject in need thereof, wherein the subject has impaired cartilage, comprising administering to the subject at the site in need of treatment an effective amount of a pharmaceutical composition comprising a growth factor bound to hyaluronic acid (HA)-based hydrogel particles, wherein the hyaluronic acid (HA)-based hydrogel particles are conjugated with a heparan sulfate proteoglycan (HSPG), wherein the growth factor is bone morphogenetic protein 2 (BMP2), wherein the heparan sulfate proteoglycan (HSPG) comprises perlecan domain 1 (PlnD1), and wherein the composition comprises 0.1-10 µg/ml of the BMP2 and 1-10 mg/ml of the hyaluronic acid (HA)-based hydrogel particles conjugated with the perlecan domain 1 (PlnD1).

2. The method of claim 1, wherein the heparan sulfate proteoglycan (HSPG) comprises the amino acid sequence of SEQ ID NO: 1.

3. The method of claim 1, wherein the growth factor is released from the hyaluronic acid (HA)-based hydrogel particles in the subject after the administration.

4. The method of claim 1, wherein the impaired cartilage is articular cartilage.

5. The method of claim 1, wherein the subject has suffered osteoarthritis, and the osteoarthritis in the subject is improved after the administration.

6. The method of claim 1, wherein the number of chondrocytes increases in the subject after the administration.

7. The method of claim 1, wherein the level of an extracellular matrix (ECM) protein in the subject is increased after the administration.

8. The method of claim 1, wherein the expression of a cartilage synthesis gene in the subject is increased after the administration.

9. The method of claim 8, wherein the cartilage synthesis gene is selected from the group consisting of type II collagen, aggrecan, perlecan, xylosyltransferase, cartilage oligomeric matrix protein (COMP), Exostosin, and type IX collagen genes.

10. The method of claim 1, wherein the expression of a cartilage degrading enzyme gene in the subject is decreased after the administration.

11. The method of claim 10, wherein the cartilage degrading enzyme gene is a gene encoding a cartilage degrading enzyme selected from the group consisting of matrix metalloproteinase 3 (Mmp3), matrix metalloproteinase 13 (Mmp13), and a disintegrin and metalloproteinase with thrombospondin motif 5 (Adamts5).

12. The method of claim 1, wherein the expression of the $\alpha$1 chain of type X collagen (Col10$\alpha$1) gene is decreased after the administration.

13. The method of claim 1, wherein the pharmaceutical composition further comprises a bioactive compound, wherein the bioactive compound is a non-steroid anti-inflammatory drug (NSAID).

14. The method of claim 1, wherein the pharmaceutical composition is administered to the subject by injection.

* * * * *